United States Patent
Smith

(10) Patent No.: US 9,526,521 B2
(45) Date of Patent: Dec. 27, 2016

(54) SURGICAL ACCESS ASSEMBLY AND METHOD OF USE THEREFOR

(71) Applicant: Covidien LP, Mansfield, MA (US)

(72) Inventor: Robert C. Smith, Chapin, SC (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 14/831,394

(22) Filed: Aug. 20, 2015

(65) Prior Publication Data

US 2015/0351795 A1    Dec. 10, 2015

Related U.S. Application Data

(63) Continuation of application No. 14/690,948, filed on Apr. 20, 2015, now Pat. No. 9,113,952, which is a
(Continued)

(51) Int. Cl.
*A61B 17/34*      (2006.01)
*A61B 17/02*      (2006.01)
(Continued)

(52) U.S. Cl.
CPC ............ *A61B 17/3423* (2013.01); *A61B 1/32* (2013.01); *A61B 17/0218* (2013.01);
(Continued)

(58) Field of Classification Search
CPC ....... A61B 1/32; A61B 17/02; A61B 17/0218; A61B 17/0281; A61B 17/0293; A61B 17/3421; A61B 17/3423; A61B 17/3431; A61B 2017/0225; A61B 2017/0287; A61B 2017/3429; A61B 2017/3443; A61B 2017/3445
(Continued)

(56) References Cited

U.S. PATENT DOCUMENTS

| 4,183,357 | A |  | 1/1980 | Bentley et al. |
| 5,159,921 | A | * | 11/1992 | Hoover ............. A61B 17/0293 600/205 |

(Continued)

FOREIGN PATENT DOCUMENTS

| EP | 0950376 A1 | 10/1999 |
| EP | 2181657 A2 | 5/2010 |

(Continued)

OTHER PUBLICATIONS

European Search Report from EP 13160771 dated Jun. 10, 2014.

*Primary Examiner* — Christian Sevilla
*Assistant Examiner* — Eric S Gibson

(57) ABSTRACT

A surgical access assembly includes an access port and a seal anchor. The access port includes a proximal ring, an intermediate ring, a distal ring, and a sleeve defining a passage therethrough. In particular, the proximal, intermediate and distal rings are concentrically arranged with the passage of the sleeve, and the sleeve extends between the proximal and distal rings. The seal anchor is adapted to be at least partially disposed in the access port, and defines a lumen therethrough. At least one of the proximal, intermediate, and distal rings is configured and dimensioned to engage the seal anchor in a sealing relation therewith.

17 Claims, 13 Drawing Sheets

Related U.S. Application Data continuation of application No. 13/782,098, filed on Mar. 1, 2013, now Pat. No. 9,017,249.

(60) Provisional application No. 61/615,498, filed on Mar. 26, 2012.

(51) Int. Cl.
*A61B 1/32* (2006.01)
*A61M 13/00* (2006.01)
*A61M 39/02* (2006.01)
*A61B 17/00* (2006.01)

(52) U.S. Cl.
CPC ....... *A61B 17/0293* (2013.01); *A61M 13/003* (2013.01); *A61M 39/0247* (2013.01); *A61B 2017/00477* (2013.01); *A61B 2017/00862* (2013.01); *A61B 2017/0225* (2013.01); *A61B 2017/3419* (2013.01); *A61B 2017/3429* (2013.01); *A61B 2017/3433* (2013.01); *A61B 2017/3443* (2013.01); *A61B 2017/3445* (2013.01); *A61B 2017/3486* (2013.01); *A61M 2039/0261* (2013.01); *A61M 2202/0225* (2013.01)

(58) Field of Classification Search
USPC .................................................. 600/201–210
See application file for complete search history.

(56) References Cited

U.S. PATENT DOCUMENTS

| | | | |
|---|---|---|---|
| 5,366,478 A | 11/1994 | Brinkerhoff et al. | |
| 5,368,545 A * | 11/1994 | Schaller | A61B 19/10 128/846 |
| 5,520,609 A * | 5/1996 | Moll | A61B 17/00234 600/204 |
| 5,524,644 A * | 6/1996 | Crook | A61B 17/0293 128/888 |
| 5,649,550 A | 7/1997 | Crook | |
| 5,788,709 A * | 8/1998 | Riek | A61B 17/00234 606/110 |
| 5,906,577 A * | 5/1999 | Beane | A61B 17/0293 600/206 |
| 6,033,428 A * | 3/2000 | Sardella | A61B 17/3423 606/213 |
| 6,254,534 B1 * | 7/2001 | Butler | A61B 1/32 600/206 |
| 6,258,024 B1 * | 7/2001 | van Der Weegen | A61B 1/32 600/114 |
| 6,382,211 B1 | 5/2002 | Crook | |
| 6,450,983 B1 | 9/2002 | Rambo | |
| 6,582,364 B2 | 6/2003 | Butler et al. | |
| 6,589,167 B1 | 7/2003 | Shimomura et al. | |
| 6,613,952 B2 * | 9/2003 | Rambo | A61B 17/0293 600/206 |
| 6,723,044 B2 * | 4/2004 | Pulford | A61B 17/0293 128/850 |
| 6,814,078 B2 * | 11/2004 | Crook | A61B 17/0293 128/849 |
| 6,846,287 B2 | 1/2005 | Bonadio et al. | |
| 6,939,296 B2 | 9/2005 | Ewers et al. | |
| 6,945,932 B1 | 9/2005 | Caldwell et al. | |
| 6,958,037 B2 * | 10/2005 | Ewers | A61B 1/32 600/208 |
| 7,033,319 B2 | 4/2006 | Pulford et al. | |
| 7,081,089 B2 | 7/2006 | Bonadio et al. | |
| 7,163,510 B2 | 1/2007 | Kahle et al. | |
| 7,195,590 B2 * | 3/2007 | Butler | A61B 17/0293 600/206 |
| 7,238,154 B2 | 7/2007 | Ewers et al. | |
| 7,344,547 B2 | 3/2008 | Piskun | |
| 7,377,898 B2 | 5/2008 | Ewers et al. | |
| 7,445,597 B2 | 11/2008 | Butler et al. | |
| 7,473,221 B2 | 1/2009 | Ewers et al. | |
| 7,540,839 B2 * | 6/2009 | Butler | A61B 17/0293 600/208 |
| 7,559,893 B2 | 7/2009 | Bonadio et al. | |
| 7,650,887 B2 | 1/2010 | Nguyen et al. | |
| 7,704,207 B2 | 4/2010 | Albrecht et al. | |
| 7,727,146 B2 * | 6/2010 | Albrecht | A61B 17/02 600/201 |
| 7,951,076 B2 | 5/2011 | Hart et al. | |
| 7,967,748 B2 * | 6/2011 | Kistler | A61B 17/3423 600/204 |
| 8,012,088 B2 | 9/2011 | Butler et al. | |
| 8,137,267 B2 * | 3/2012 | Shelton, IV | A61B 17/3423 600/203 |
| 8,187,178 B2 | 5/2012 | Bonadio et al. | |
| 8,192,358 B2 * | 6/2012 | Leahy | A61B 17/3423 600/207 |
| 8,231,527 B2 * | 7/2012 | Beckman | A61B 17/0293 600/206 |
| 8,343,047 B2 * | 1/2013 | Albrecht | A61B 1/32 600/206 |
| 8,353,824 B2 * | 1/2013 | Shelton, IV | A61B 17/3423 600/208 |
| 8,357,085 B2 | 1/2013 | Shelton, IV et al. | |
| 8,414,485 B2 | 4/2013 | Richard et al. | |
| 8,550,992 B2 | 10/2013 | Kleyman | |
| 8,574,153 B2 | 11/2013 | Richard | |
| 8,602,983 B2 * | 12/2013 | Kleyman | A61B 17/3423 600/208 |
| 8,764,645 B2 * | 7/2014 | Kleyman | A61B 17/3423 600/204 |
| 8,764,765 B2 * | 7/2014 | Piskun | A61B 17/29 600/112 |
| 8,845,529 B2 * | 9/2014 | Smith | A61B 17/3423 600/207 |
| 9,017,249 B2 | 4/2015 | Smith | |
| 2001/0037053 A1 * | 11/2001 | Bonadio | A61B 17/0293 600/208 |
| 2003/0139767 A1 | 7/2003 | Jespersen | |
| 2003/0187376 A1 | 10/2003 | Rambo | |
| 2003/0192553 A1 * | 10/2003 | Rambo | A61B 17/0293 128/850 |
| 2004/0092795 A1 | 5/2004 | Bonadio et al. | |
| 2004/0154624 A1 * | 8/2004 | Bonadio | A61B 17/0293 128/849 |
| 2004/0267096 A1 * | 12/2004 | Caldwell | A61B 17/3423 600/213 |
| 2005/0020884 A1 * | 1/2005 | Hart | A61B 17/0293 600/206 |
| 2005/0090717 A1 * | 4/2005 | Bonadio | A61B 17/0293 600/208 |
| 2005/0148823 A1 * | 7/2005 | Vaugh | A61B 17/0293 600/206 |
| 2005/0192483 A1 * | 9/2005 | Bonadio | A61B 17/3423 600/208 |
| 2005/0241647 A1 * | 11/2005 | Nguyen | A61B 17/0293 128/856 |
| 2005/0288558 A1 | 12/2005 | Ewers et al. | |
| 2006/0084842 A1 | 4/2006 | Hart et al. | |
| 2006/0149137 A1 * | 7/2006 | Pingleton | A61B 1/32 600/208 |
| 2006/0161049 A1 * | 7/2006 | Beane | A61B 17/0293 600/207 |
| 2006/0161050 A1 | 7/2006 | Butler et al. | |
| 2006/0247498 A1 * | 11/2006 | Bonadio | A61M 13/003 600/208 |
| 2007/0093695 A1 * | 4/2007 | Bonadio | A61B 17/3423 600/208 |
| 2007/0118175 A1 | 5/2007 | Butler et al. | |
| 2007/0151566 A1 * | 7/2007 | Kahle | A61B 17/3423 128/856 |
| 2007/0162067 A1 | 7/2007 | Lunsford et al. | |
| 2007/0203398 A1 | 8/2007 | Bonadio et al. | |
| 2007/0208312 A1 | 9/2007 | Norton et al. | |
| 2007/0270654 A1 | 11/2007 | Pignato et al. | |

(56) References Cited

U.S. PATENT DOCUMENTS

| | | | |
|---|---|---|---|
| 2008/0021360 A1* | 1/2008 | Fihe | A61B 17/0293 602/60 |
| 2008/0021362 A1* | 1/2008 | Fihe | A61B 17/0293 602/75 |
| 2008/0097163 A1 | 4/2008 | Butler et al. | |
| 2009/0221966 A1* | 9/2009 | Richard | A61B 17/3421 604/164.04 |
| 2010/0113883 A1* | 5/2010 | Widenhouse | A61B 17/3423 600/208 |
| 2010/0240960 A1* | 9/2010 | Richard | A61B 17/3423 600/208 |
| 2010/0249516 A1* | 9/2010 | Shelton, IV | A61B 17/0293 600/203 |
| 2010/0249520 A1 | 9/2010 | Shelton, IV et al. | |
| 2010/0249521 A1 | 9/2010 | Shelton, IV et al. | |
| 2010/0249525 A1* | 9/2010 | Shelton, IV | A61B 17/3423 600/208 |
| 2010/0261972 A1* | 10/2010 | Widenhouse | A61B 17/3462 600/206 |
| 2010/0261973 A1 | 10/2010 | Mollenauer et al. | |
| 2010/0261974 A1 | 10/2010 | Shelton, IV et al. | |
| 2010/0262080 A1* | 10/2010 | Shelton, IV | A61B 17/3423 604/164.09 |
| 2010/0280326 A1* | 11/2010 | Hess | A61B 17/3423 600/206 |
| 2010/0286484 A1* | 11/2010 | Stellon | A61B 17/3423 600/208 |
| 2010/0312066 A1* | 12/2010 | Cropper | A61B 17/3423 600/207 |
| 2011/0054258 A1* | 3/2011 | O'Keefe | A61B 17/3423 600/206 |
| 2011/0054260 A1* | 3/2011 | Albrecht | A61B 17/0218 600/208 |
| 2011/0125186 A1* | 5/2011 | Fowler | A61B 17/3423 606/213 |
| 2011/0201883 A1* | 8/2011 | Cooper | A61B 17/3421 600/109 |
| 2011/0251463 A1* | 10/2011 | Kleyman | A61B 17/3421 600/205 |
| 2011/0251464 A1* | 10/2011 | Kleyman | A61B 17/3423 600/206 |
| 2012/0083660 A1* | 4/2012 | Okoniewski | A61B 17/3423 600/207 |
| 2012/0130177 A1* | 5/2012 | Davis | A61B 17/3423 600/201 |
| 2012/0157779 A1* | 6/2012 | Fischvogt | A61B 17/0293 600/207 |
| 2012/0157781 A1* | 6/2012 | Kleyman | A61B 17/3423 600/208 |
| 2012/0157783 A1* | 6/2012 | Okoniewski | A61B 17/3423 600/208 |
| 2012/0157786 A1* | 6/2012 | Pribanic | A61B 17/0293 600/208 |
| 2012/0190933 A1* | 7/2012 | Kleyman | A61B 17/3423 600/207 |
| 2012/0209078 A1 | 8/2012 | Pribanic et al. | |
| 2012/0238825 A1* | 9/2012 | Smith | A61B 17/3423 600/207 |
| 2012/0245427 A1 | 9/2012 | Kleyman | |
| 2012/0245428 A1* | 9/2012 | Smith | A61B 17/3423 600/208 |
| 2012/0245429 A1* | 9/2012 | Smith | A61B 17/0218 600/208 |
| 2012/0245430 A1 | 9/2012 | Kleyman et al. | |
| 2012/0253134 A1* | 10/2012 | Smith | A61B 17/3423 600/203 |
| 2012/0253136 A1* | 10/2012 | Rodrigues, Jr. | A61B 17/3423 600/208 |
| 2012/0283520 A1 | 11/2012 | Kleyman | |
| 2013/0060094 A1* | 3/2013 | Lee | A61B 17/0293 600/207 |
| 2013/0066156 A1* | 3/2013 | Seo | A61B 17/3423 600/204 |
| 2013/0172681 A1* | 7/2013 | Smith | A61B 17/3423 600/203 |
| 2013/0190573 A1* | 7/2013 | Smith | A61B 17/0218 600/207 |
| 2013/0190574 A1* | 7/2013 | Smith | A61B 17/0218 600/208 |
| 2013/0225930 A1* | 8/2013 | Smith | A61B 1/24 600/204 |
| 2013/0225932 A1* | 8/2013 | Smith | A61B 1/313 600/206 |
| 2013/0253277 A1* | 9/2013 | Smith | A61B 1/32 600/204 |
| 2013/0253278 A1* | 9/2013 | Smith | A61B 17/3423 600/204 |
| 2013/0253279 A1* | 9/2013 | Smith | A61B 17/3423 600/204 |

FOREIGN PATENT DOCUMENTS

| | | |
|---|---|---|
| EP | 2238933 A1 | 10/2010 |
| WO | 96/10963 | 4/1996 |
| WO | 00/32116 | 6/2000 |
| WO | 00/54675 | 9/2000 |
| WO | 01/91652 A1 | 12/2001 |
| WO | 2004/075741 A2 | 9/2004 |
| WO | 2006/110733 | 10/2006 |
| WO | 2010/141673 | 12/2010 |

* cited by examiner

SURGICAL ACCESS ASSEMBLY AND METHOD OF USE THEREFOR

CROSS REFERENCE TO RELATED APPLICATION

This application is a continuation of U.S. patent application Ser. No. 14/690,948, filed Apr. 20, 2015, which is a continuation of U.S. patent application Ser. No. 13/782,098, filed Mar. 1, 2013, now U.S. Pat. No. 9,017,249, which claims priority to and the benefit of U.S. Provisional Patent Application No. 61/615,498, filed Mar. 26, 2012, the entire contents of each of which are hereby incorporated by reference.

BACKGROUND

Technical Field

The present disclosure relates to a surgical access assembly, and more particularly, to a surgical access assembly including an access port and a seal anchor adaptably engaging each other in a sealing relation and a method of use therefor.

Background of Related Art

Various surgical procedures are performed in a minimally invasive manner. This includes forming a small opening through a body wall of the patient, e.g., in the abdomen, and inserting a seal anchor through the opening to provide a substantially fluid-tight seal between a body cavity of a patient and the atmosphere. Due to the relatively small interior dimensions of the access devices used in endoscopic procedures, only the elongated, small diametered instrumentation such as, e.g., trocar and cannula assemblies, may be used to access the internal body cavities and organs. In general, prior to the introduction of the surgical object into the patient's body, insufflation gases are used to enlarge the area surrounding the target surgical site to create a larger, more accessible work area.

When compared to the larger incisions typically found in traditional procedures, both trauma to the patient and recovery time are reduced for procedures involving small incisions. However, minimally invasive surgery such as, e.g., laparoscopy, has several limitations. In particular, surgery of this type requires a great deal of skill in manipulating the long narrow endoscopic instruments to a remote site under endoscopic visualization. To this end, hand-assisted laparoscopic techniques and procedures have been developed. These procedures include both laparoscopic and conventional surgical methodologies. The hand-assisted technique is performed utilizing a seal anchor in conjunction with an access port, which is an enlarged device that protects the incised opening from, for example, infection and contamination.

The maintenance of a substantially fluid-tight seal is desirable to prevent the escape of the insufflation gases and the deflation or collapse of the enlarged surgical site. Accordingly, there is a need for an access assembly used in a hand-assisted minimally invasive procedure that can accommodate a variety of surgical objects while maintaining the integrity of an insufflated workspace.

SUMMARY

In accordance with an embodiment of the present disclosure, there is provided a surgical access assembly including an access port and a seal anchor. The access port includes a proximal ring, an intermediate ring, a distal ring, and a sleeve defining a passage therethrough. In particular, the proximal, intermediate and distal rings are concentrically arranged with the passage of the sleeve. The sleeve extends between the proximal and distal rings. The seal anchor is adapted to be disposed in the access port. The seal anchor defines a lumen therethrough, wherein at least one of the proximal, intermediate and distal rings is configured and dimensioned to engage the seal anchor in a sealing relation therewith.

The seal anchor may define a circumferential groove dimensioned and configured to receive one of the proximal, intermediate, and distal rings. The proximal ring may have a kidney-shaped cross-section and the sleeve may be rollable about the proximal ring. The distal ring may have a diameter smaller than that of the seal anchor. The distal ring may be adapted to engage the seal anchor in a sealing relation therewith. In particular, the distal ring may be an O-ring. Furthermore, the O-ring may be an inflatable balloon. In addition, the intermediate ring may have a kidney-shaped cross-section, in which case the proximal ring may be adapted to engage the seal anchor in a sealing relation therewith. The proximal ring may be an O-ring.

In an embodiment, the intermediate ring may be slidably disposed on an outer surface of the sleeve. In particular, the diameters of the proximal and distal rings may be larger than that of the intermediate ring. Furthermore, the intermediate ring may be adapted to engage the seal anchor in a sealing relation therewith. The proximal member may have a kidney-shaped cross-section. The sleeve may be rollable about the proximal ring.

The proximal, distal, and intermediate rings may be elastic. The sleeve may be made of an elastic material. The seal anchor may be a compressible material. The lumen defined in the seal anchor may be dimensioned to receive surgical instruments therethrough. At least one of the proximal, distal, or intermediate ring may be an inflatable balloon.

In accordance with another aspect of the present disclosure, there is provided a method of accessing an internal body cavity. The method includes providing a surgical access assembly including an access port and a seal anchor. In particular, the access port has a proximal ring, an intermediate ring, a distal ring, and a sleeve defining a passage therethrough. The proximal, intermediate and distal rings are concentrically arranged with the passage of the sleeve, and the sleeve extends between the proximal and distal rings. In addition, the seal anchor is adapted to be disposed in the access port. The method further includes positioning at least one of the proximal, intermediate, and distal rings of the access port into the body cavity, rolling the sleeve of the access port such that at least two of the proximal, distal and intermediate rings engage an internal peritoneal wall of tissue and an outer epidermal tissue, positioning the seal anchor within the access port and introducing a surgical instrument to the body cavity through the seal anchor.

The sleeve may be rollable about the proximal ring. The proximal ring may have a kidney-shaped cross-section. The distal ring may be adapted to engage the seal anchor in a sealing relation therewith. The sleeve may be rollable about the intermediate ring, in which case the proximal ring may be adapted to engage the seal anchor in a sealing relation therewith.

In an embodiment, positioning the seal anchor within the access port may include engaging at least one of the proximal, intermediate, and distal rings with the seal anchor in a sealing relation therewith. It is further contemplated that the method may further include insufflating the body cavity.

BRIEF DESCRIPTION OF THE DRAWINGS

Various embodiments of the present disclosure are described hereinbelow with reference to the drawings, wherein.

DETAILED DESCRIPTION OF EMBODIMENTS

Figure 1:
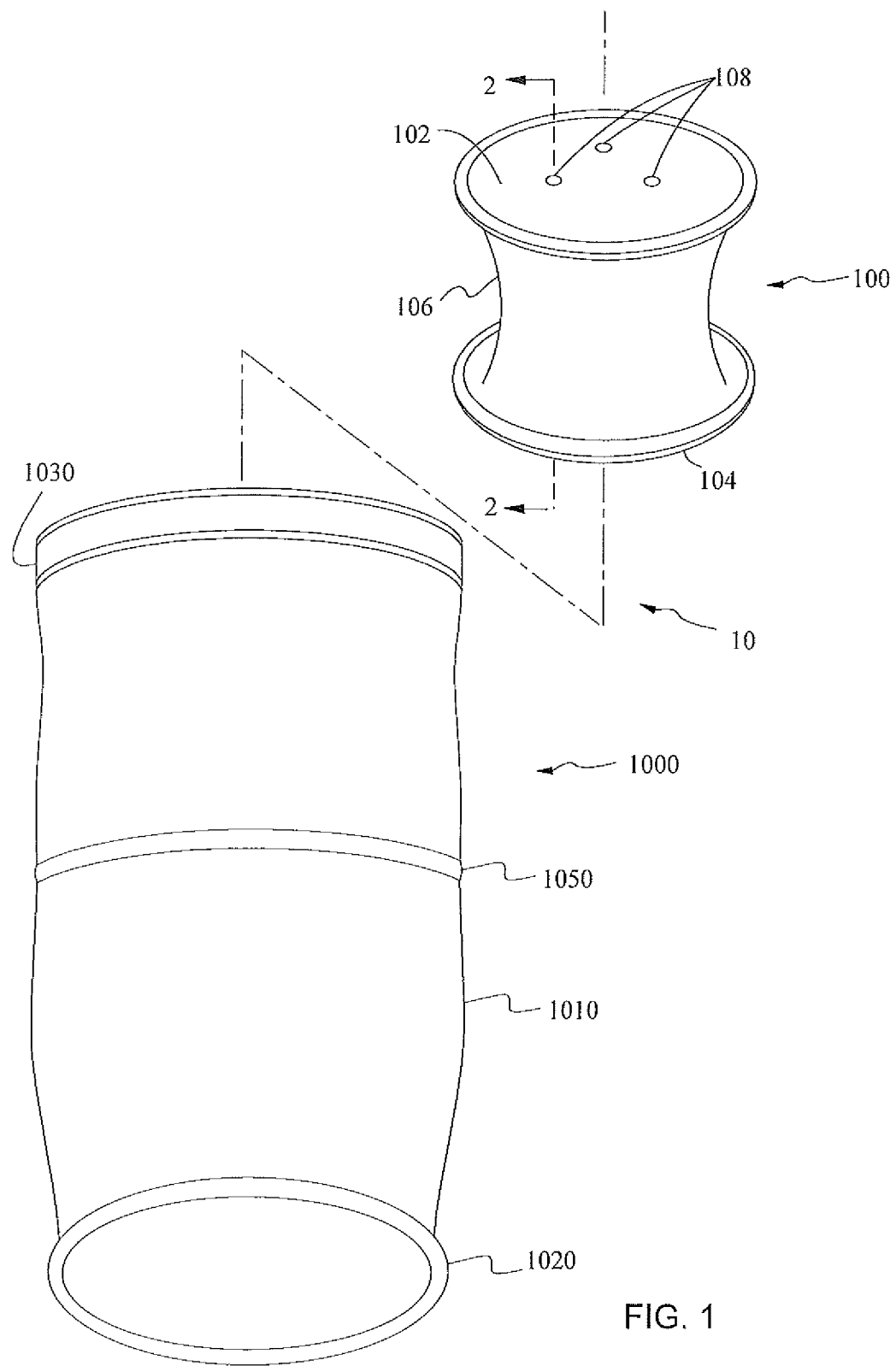
FIG. 1 is a perspective view of a surgical access assembly in accordance with an embodiment of the present disclosure.

Embodiments of the present disclosure will now be described in detail with reference to the drawings, in which like reference numerals designate identical or corresponding elements in each of the several views. As used herein, the term "distal," as is conventional, will refer to that portion of the instrument, apparatus, device or component thereof which is farther from the user while, the term "proximal," will refer to that portion of the instrument, apparatus, device or component thereof which is closer to the user. In the following description, well-known functions or constructions are not described in detail to avoid obscuring the present disclosure in unnecessary detail.

With reference to FIG. 1, there is illustrated a surgical access assembly 10 in accordance with an embodiment of the present disclosure. Surgical access assembly 10 includes a seal anchor 100 and an access port 1000. Access port 1000 is adapted for insertion within a tissue tract, e.g., through an opening in the abdominal or peritoneal lining, as well as a naturally occurring orifice. Access port 1000 protects the opening from, for example, infection and contamination. In addition, access port 1000 may serve to retract the opening, as will be discussed below. Seal anchor 100 is disposed in access port 1000 in a sealing relation therewith to provide a substantially fluid-tight seal between a body cavity of a patient and the atmosphere. Both access port 1000 and seal anchor 100, however, may be used as a stand-alone device for insertion of endoscopic instruments.

With continued reference to FIG. 1, seal anchor 100 is configured to receive surgical instruments of varying diameter therethrough. Seal anchor 100 is formed from elastic/compressible type material having sufficient compliance to form a seal about a surgical object and to establish a sealing relation with access port 1000. Furthermore, such material enables seal anchor 100 to accommodate off-axis motion of the surgical object extending therethrough.

Seal anchor 100 contemplates introduction of various types of instrumentation adapted for insertion through a trocar and/or cannula assembly while maintaining a substantially fluid-tight interface about the instrument to help preserve the atmospheric integrity of a surgical procedure from gas and/or fluid leakage. Examples of instrumentation include, but are not limited to, clip appliers, graspers, dissectors, retractors, staplers, laser probes, photographic devices, endoscopes and laparoscopes, tubes, and the like. Such instruments will collectively be referred to as "instruments" or "instrumentation."

Figure 2:
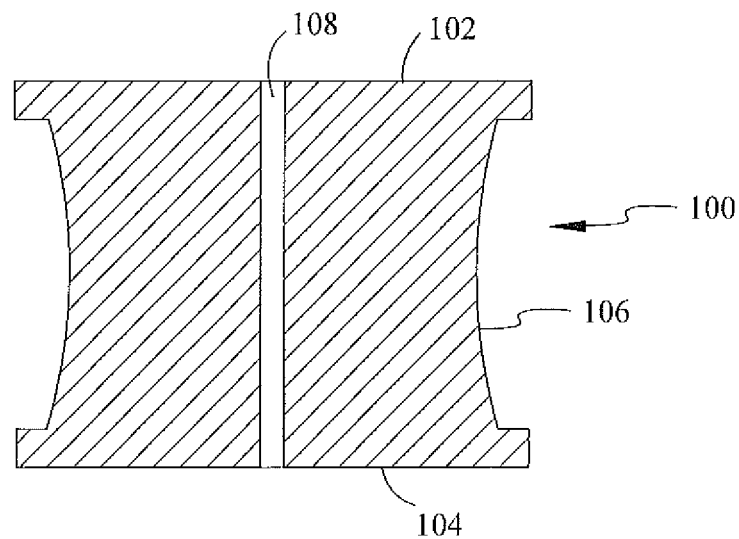
FIG. 2 is a longitudinal cross-sectional view of a seal anchor of the surgical access assembly of FIG. 1 taken along section line 2-2 of FIG. 1 illustrating a longitudinally extending lumen of the seal anchor.

With reference now to FIG. 2, seal anchor 100 includes proximal and distal end portions 102, 104 and an intermediate portion 106 extending between proximal and distal end portions 102, 104. Seal anchor 100 defines at least one lumen or channel 108 that extends longitudinally between proximal and distal end portions 102, 104. Proximal and distal end portions 102, 104 define substantially planar surfaces. However, proximal and distal end portions 102, 104 may define surfaces that are substantially arcuate to assist in the insertion of seal anchor 100 within tissue. The radial dimension of intermediate portion 106 is appreciably less than those of respective proximal and distal end portions 102, 104. Under such configuration, seal anchor 100 defines an hourglass shape or profile to assist in anchoring seal anchor 100 within tissue when seal anchor 100 is used as a stand-alone device.

Seal anchor 100 is adapted to transition from an expanded condition to a deformed condition to facilitate insertion and securement of the surgical instruments in tissue. Seal anchor 100 is formed of a biocompatible compressible material that facilitates the resilient, reciprocal transitioning of seal anchor 100 between the expanded and deformed conditions thereof. Seal anchor 100 is biased to the initial condition, and thus in the absence of any force applied to seal anchor 100, seal anchor 100 is in the expanded condition.

Figure 8:
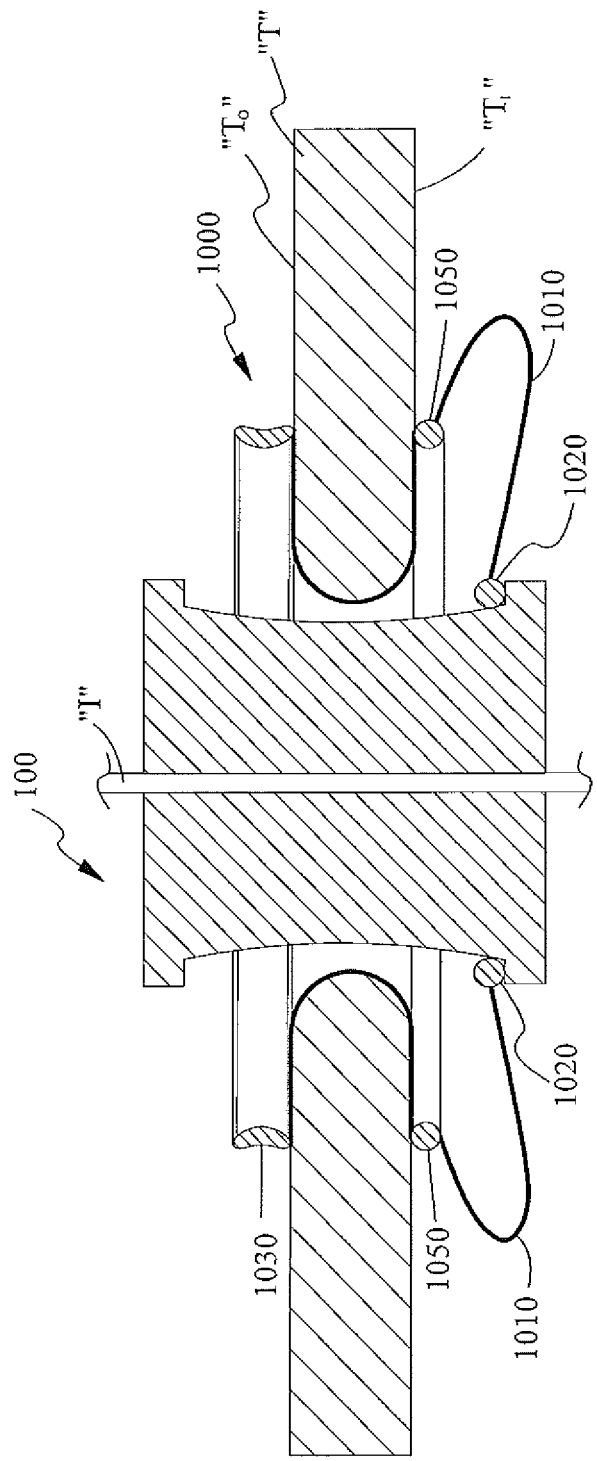
FIG. 8 is a longitudinal cross-sectional view of the surgical access assembly of FIG. 1 secured to tissue.

Lumen 108 is configured to removably receive a surgical object "I" (FIG. 8). Prior to the insertion of surgical object "I," lumen 108 is in a first state in which lumen 108 defines a first or initial dimension that substantially prevents escape of insufflation gas through lumen 108 in the absence of surgical object "I." Upon insertion of surgical object "I" through lumen 108, lumen 108 transitions to a second state in which lumen 108 defines a second, larger dimension that substantially approximates the diameter of surgical object "I" such that a substantially fluid-tight seal is formed with surgical object "I." In particular, the compressible material comprising seal anchor 100 facilitates the resilient transitioning of lumen 108 between its first state and its second state. An example of a seal anchor is disclosed in a commonly assigned U.S. patent application Ser. No. 12/939,204, filed on Nov. 4, 2010, the entire contents of which are fully incorporated herein by reference.

Figure 3:
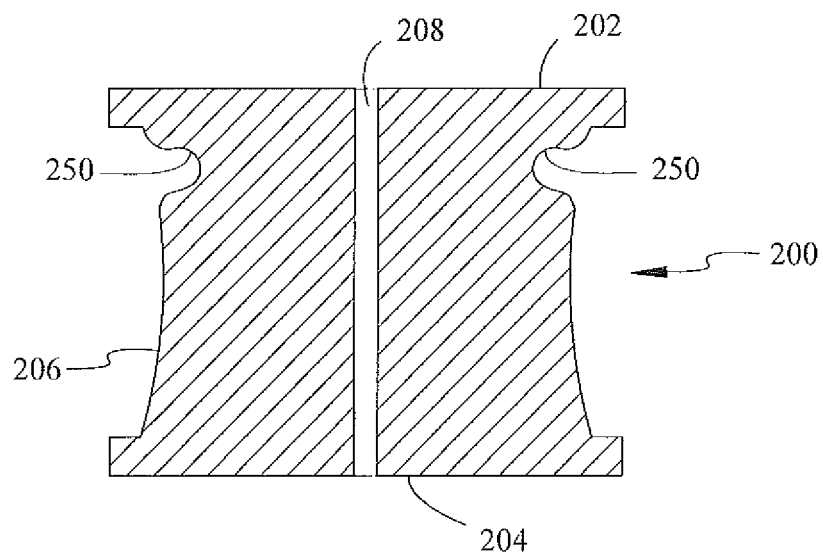
FIG. 3 is a longitudinal cross-sectional view of a seal anchor in accordance with another embodiment of the present disclosure.

With reference now to FIG. 3, a seal anchor 200 in accordance with an embodiment of the present disclosure is illustrated. In the interest of brevity, the present embodiment will focus on the differences between the previously described seal anchor 100 and seal anchor 200. Seal anchor 200 includes proximal and distal end portions 202, 204 and an intermediate portion 206 extending between proximal and distal end portions 202, 204. Proximal and distal end portions 202, 204 define substantially planar surfaces. Intermediate portion 206 defines a lumen 208 extending therethrough. In contrast to seal anchor 100, seal anchor 200 defines a circumferential groove 250 in intermediate portion 206. In particular, circumferential groove 250 is adjacent proximal end portion 202 of seal anchor 200. Circumferential groove 250 engages access port 1000 and facilitates sealing relation and securement therewith, as will be described in detail hereinbelow.

Figure 4:
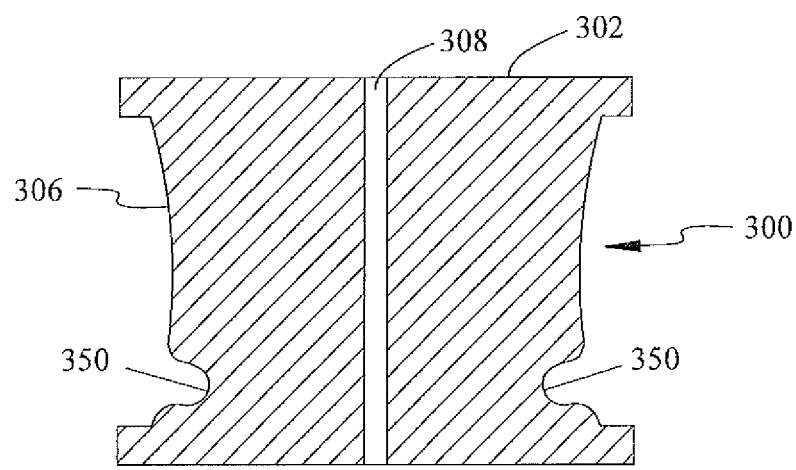
FIG. 4 is a longitudinal cross-sectional view of a seal anchor in accordance with still another embodiment of the present disclosure.
Figure 5:
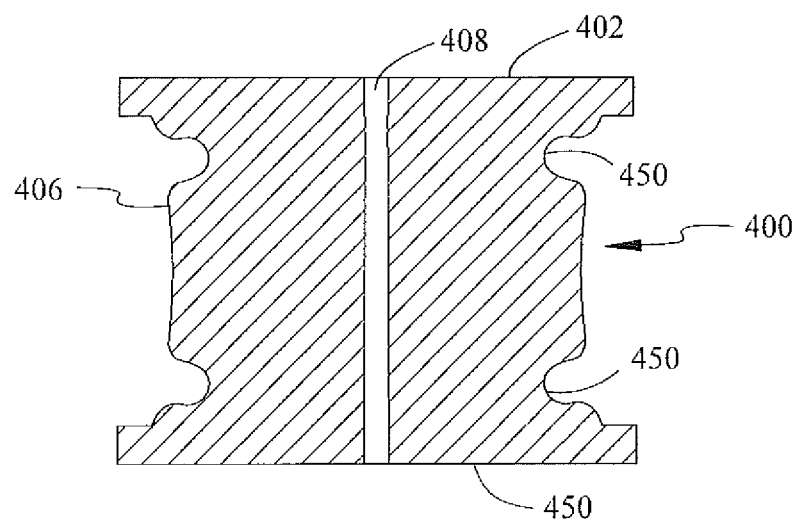
FIG. 5 is a longitudinal cross-sectional view of a seal anchor in accordance with still yet another embodiment of the present disclosure.

It is further contemplated that a circumferential groove 250 may be defined at any longitudinal position along a length of intermediate portion 206. For example, a seal anchor 300 may define a circumferential groove 350 in an intermediate portion 306 adjacent a distal end portion 304, as illustrated in FIG. 4. In addition, it is further envisioned that a seal anchor 400 may define a plurality of circumferential grooves 450 along a length of intermediate portion 406, as shown in FIG. 5.

Figure 6:
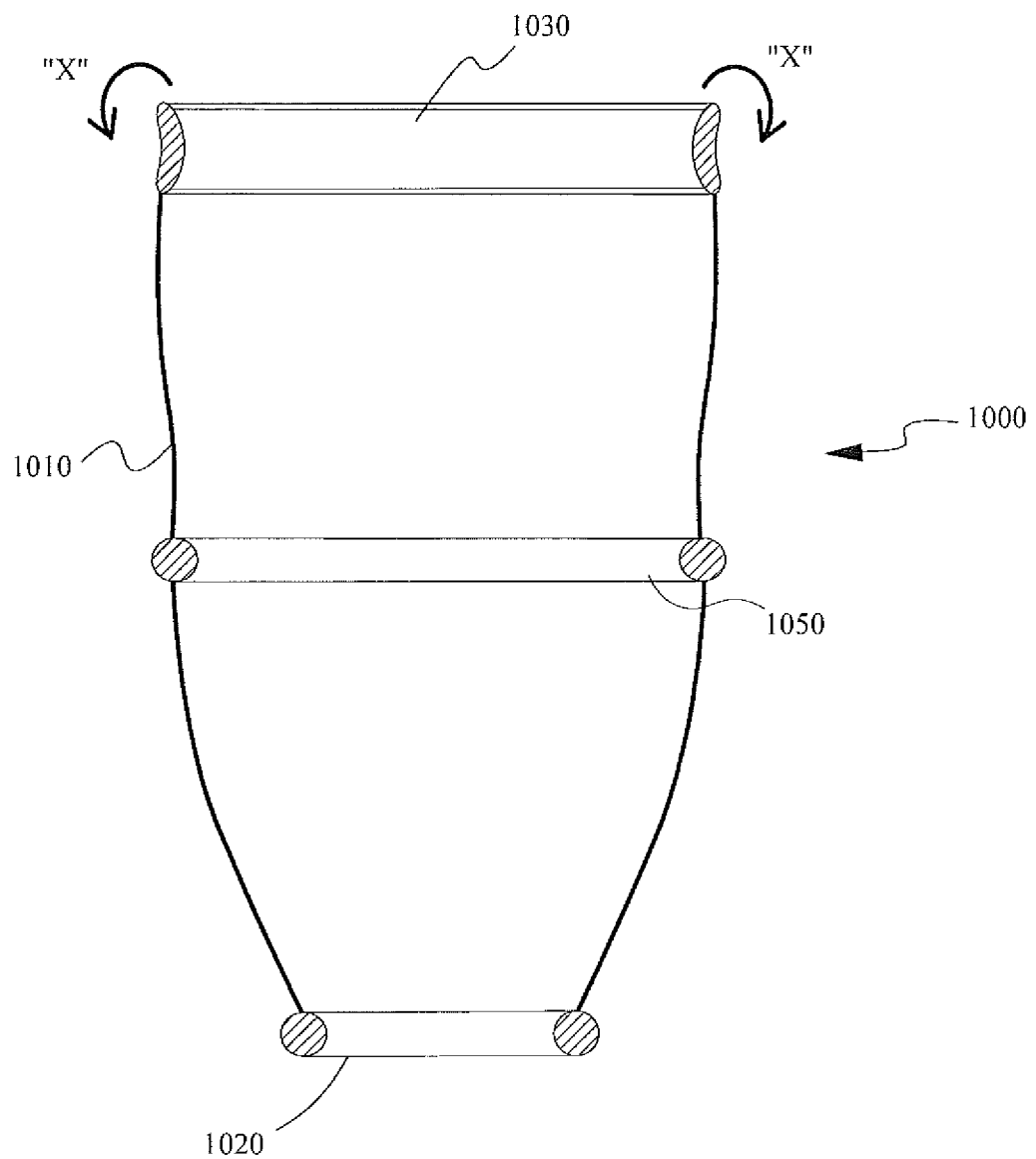
FIG. 6 is a longitudinal cross-sectional view of an access port of the surgical access assembly of FIG. 1.

With particular reference now to FIG. 6, access port 1000 includes a distal ring 1020, a proximal ring 1030, an intermediate ring 1050, and a flexible sleeve 1010 defining a passage therethrough. Distal, proximal and intermediate rings 1020, 1030, 1050 are concentrically arranged and are longitudinally connected to sleeve 1010.

Distal, proximal and intermediate rings 1020, 1030, 1050 are formed of relatively flexible materials to facilitate compression and expansion of distal, proximal, and intermediate rings 1020, 1030, 1050. For example, distal, proximal, and intermediate rings 1020, 1030, 1050 may be made from an elastomer such as polyurethane, polyethylene, silicone, and the like. The resilient nature of distal, proximal, and intermediate rings 1020, 1030, 1050 allows distal, proximal, and intermediate rings 1020, 1030, 1050 to return to their normal, substantially annular configuration.

In particular, proximal and intermediate rings 1030, 1050 are adapted to engage the walls defining the body cavity. Intermediate ring 1050 engages the internal peritoneal wall $T_I$, and proximal ring 1030 engages the outer epidermal tissue $T_O$ (FIG. 8). Distal ring 1020 is adapted to engage intermediate portion 106 of seal anchor 100 in a sealing relation therewith. Thus, in order to provide a fluid-tight seal against intermediate portion 106 of seal anchor 100, distal ring 1020 may have a diameter smaller than that of intermediate portion 106. In addition, distal ring 1020 is adapted and dimensioned to be disposed in circumferential groove 250, 350, 450 of seal anchors 200, 300, 400 to improve securement therewith.

Sleeve 1010 has elastomeric properties to facilitate securement of access port 1000 to the incision. Proximal ring 1030 is rollable to gather flexible sleeve 1010 around proximal ring 1030. For example, proximal ring 1030 is rollable, e.g., in the outward direction (as shown by arrow "X" in FIG. 6) to shorten sleeve 1010 and in the inward direction to lengthen the sleeve 1010, or vice versa. Sleeve 1010 may be shortened such that proximal ring 1030 engages the outer epidermal tissue $T_O$ adjacent the incision in tissue "T," and intermediate ring 1050 positioned in the body cavity engages the internal peritoneal wall $T_I$ (FIG. 8). In this manner, access port 1000 is securely fixed to tissue "T."

With continued reference to FIG. 6, proximal ring 1030 has a kidney-shaped cross-sectional profile. Kidney-shaped cross-section facilitates rolling of sleeve 1010 about proximal ring 1030 and inhibits unrolling of sleeve 1010 over proximal ring 1030 by providing a flattened edge disposed on the outer epidermal tissue $T_O$. Intermediate and distal rings 1050, 1020, on the other hand, may be an O-ring having a circular cross-section. However, other cross-sectional profiles are also contemplated for proximal, intermediate, and distal rings 1030, 1050, 1020. It is also envisioned that the O-ring may be an inflatable balloon.

In addition, proximal and intermediate rings 1030, 1050 can vary in size. For example, the dimensions of proximal and intermediate rings 1030, 1050 may be selectively chosen to be greater than that of a desired opening, as shown in FIG. 8. In this manner, proximal and intermediate rings 1030, 1050 may have sufficient footing to maintain elastic sleeve 1010 that has been stretched and retained at a distance greater than the natural distance.

By having dimensions of proximal and intermediate rings 1030, 1050 larger than that of the desired the opening in tissue "T," access port 1000 is adapted to dilate the opening to a desired dimension. More retraction is possible through shortening of sleeve 1010 by rolling proximal ring 1030 outward, in the direction of arrow "X," while less retraction is possible by rolling proximal ring 1030 inward.

In use, the peritoneal cavity (not shown) is insufflated with a suitable biocompatible gas such as, e.g., $CO_2$ gas, such that the cavity wall is raised and lifted away from the internal organs and tissue housed therein, thereby providing greater access thereto. The insufflation may be performed with an insufflation needle or similar device, as is conventional in the art. Either prior or subsequent to insufflation, an incision is made in tissue "T," the dimensions of which may be varied dependent upon the nature of the procedure.

Figure 7:
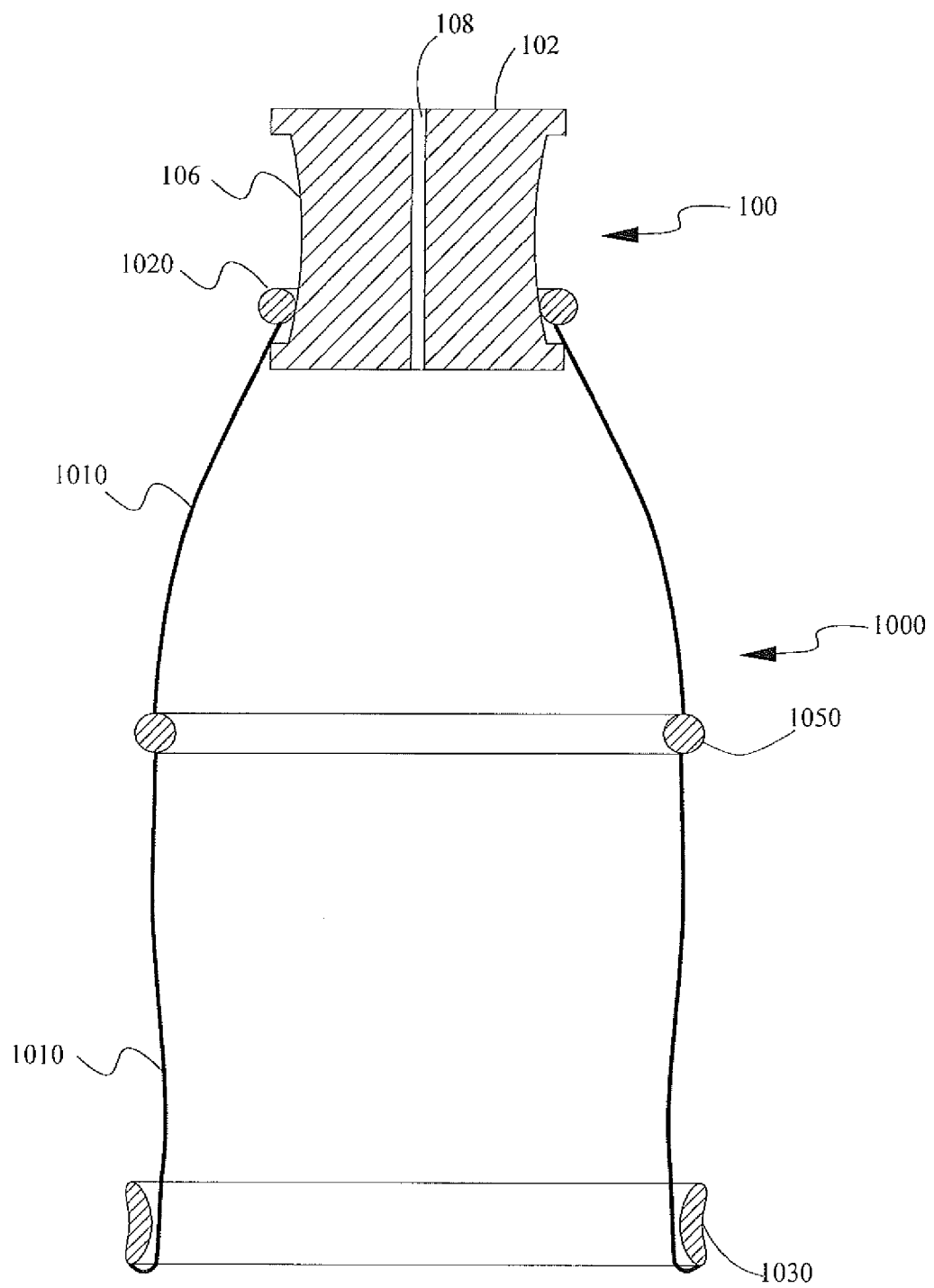
FIG. 7 is longitudinal cross-sectional views of the access port of FIG. 6 in a sealing relation with the seal anchor of FIG. 2.

Prior to the insertion of access port 1000 within tissue, distal and intermediate rings 1020, 1050 are pulled proximally through proximal ring 1030, as shown in FIG. 7. At this time, distal ring 1020 is positioned around intermediate portion 106 of seal anchor 100. Distal ring 1020 having a smaller diameter than that of intermediate portion 106 of seal anchor 100 provides a sealing relation therewith. (As discussed hereinabove, seal anchors 200, 300, 400 may be used in place of seal anchor 100, in which case distal ring 1020 is disposed in circumferential groove 250, 350, 450 of seal anchors 200, 300, 400 to facilitate securement thereof with seal anchor 200, 300, 400).

Access port 1000 is in its expanded condition which inhibits the insertion thereof into tissue tract. To facilitate insertion, the user transitions intermediate and distal rings 1050, 1020 into the compressed condition by, e.g., squeezing intermediate and distal rings 1050, 1020, along with distal end portion 104 of seal anchor 100. Intermediate and distal rings 1050, 1020, along with a portion of seal anchor 100 are inserted through proximal ring 1030 and into the opening in tissue "T." Subsequent to its insertion, distal and intermediate rings 1020, 1050 are disposed beneath tissue "T."

At this time, proximal ring 1030 may be rolled in the direction of arrow "X," as shown in FIG. 6, such that intermediate ring 1050 engages the internal peritoneal wall $T_I$ and proximal ring 1030 engages the outer epidermal tissue $T_O$ to secure access port 1000 within the opening in tissue "T," as shown in FIG. 8. Depending on the nature of the procedure being performed, the opening in tissue "T"

may be retracted by rolling sleeve 1010 about proximal ring 1030. At this time, proximal ring 1030 engages the outer epidermal tissue $T_O$ in a sealing relation therewith, and intermediate ring 1050 engages the internal peritoneal wall $T_I$ in a sealing relation therewith. A portion of sleeve 1010 that connects distal and intermediate rings 1020, 1050 provides a substantially fluid-tight seal between the body cavity of the patient and the atmosphere, as shown in FIG. 8.

Prior to the insertion of surgical object "I," lumen 108 defines a first or initial dimension that substantially prevents escape of insufflation gas through lumen 108 in the absence of surgical object "I." Upon insertion of surgical object "I" through lumen 108, lumen 108 transitions to a second state in which lumen 108 defines a second, larger dimension that substantially approximates the diameter of surgical object "I" such that a substantially fluid-tight seal is formed with surgical object "I."

One or more surgical objects "I" may be inserted through lumen 108 of seal anchor 100. With surgical instruments "I" inserted through lumen 108 and into the body cavity of the patient, the user may swivel or rotate surgical instrument "I" to a desired orientation with respect to tissue "T." At this time, access assembly 10 provides a fluid-tight seal between a body cavity of a patient and the atmosphere. During the surgical procedure, surgical instrument "I" and seal anchor 100 may be removed from access port 1000, to enable passage of the surgeon's hand through the opening in tissue "T" to access the body cavity of the patient, if needed. Distal ring 1020 may surround, e.g., the arm of the surgeon, to provide a fluid-tight seal against the arm. Upon completing the surgical procedure, the user may remove the surgical access assembly 10 from the incision of the patient.

Figure 9:
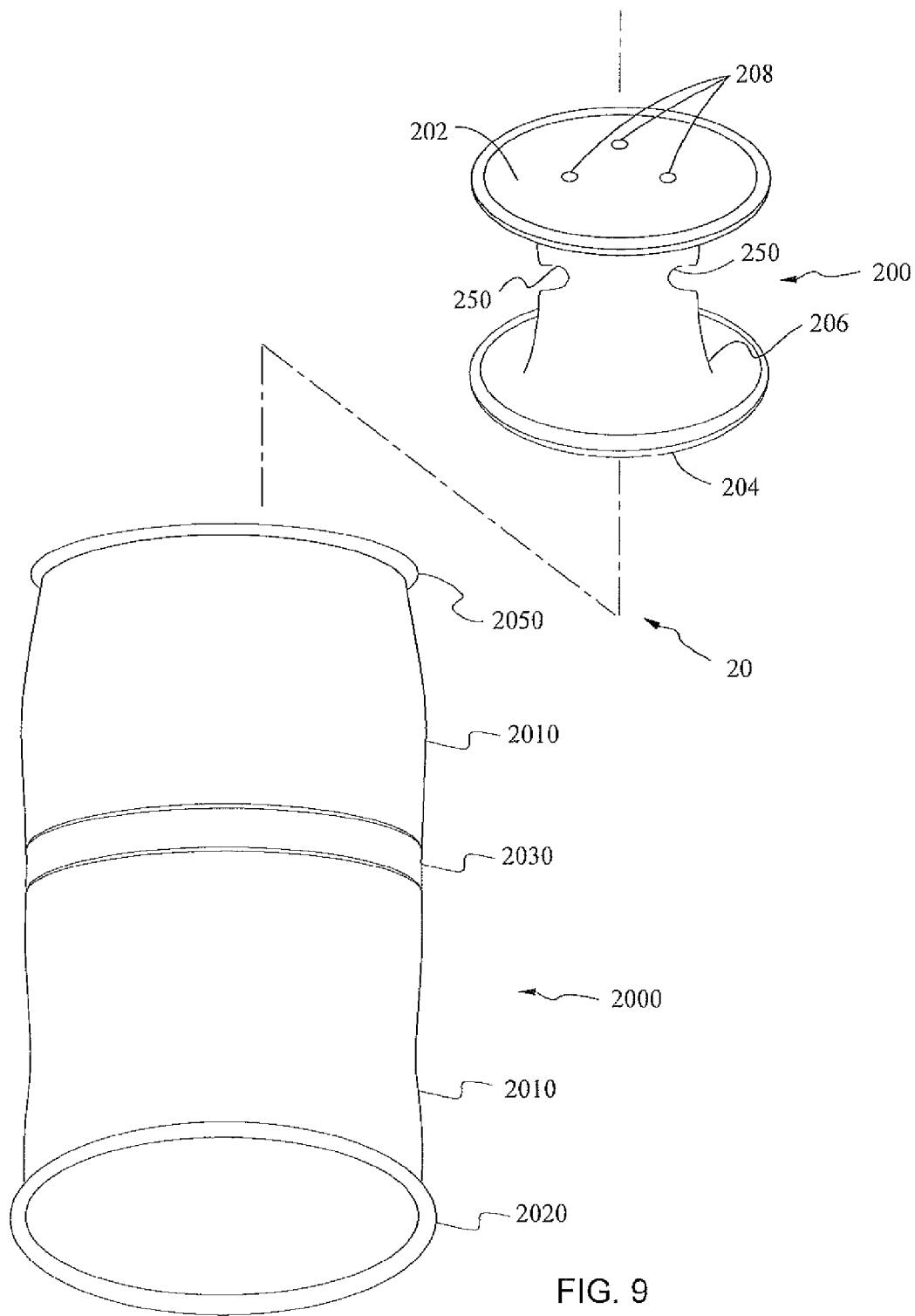
FIG. 9 is a perspective view of a surgical access assembly in accordance with another embodiment of the present disclosure.
Figure 10:
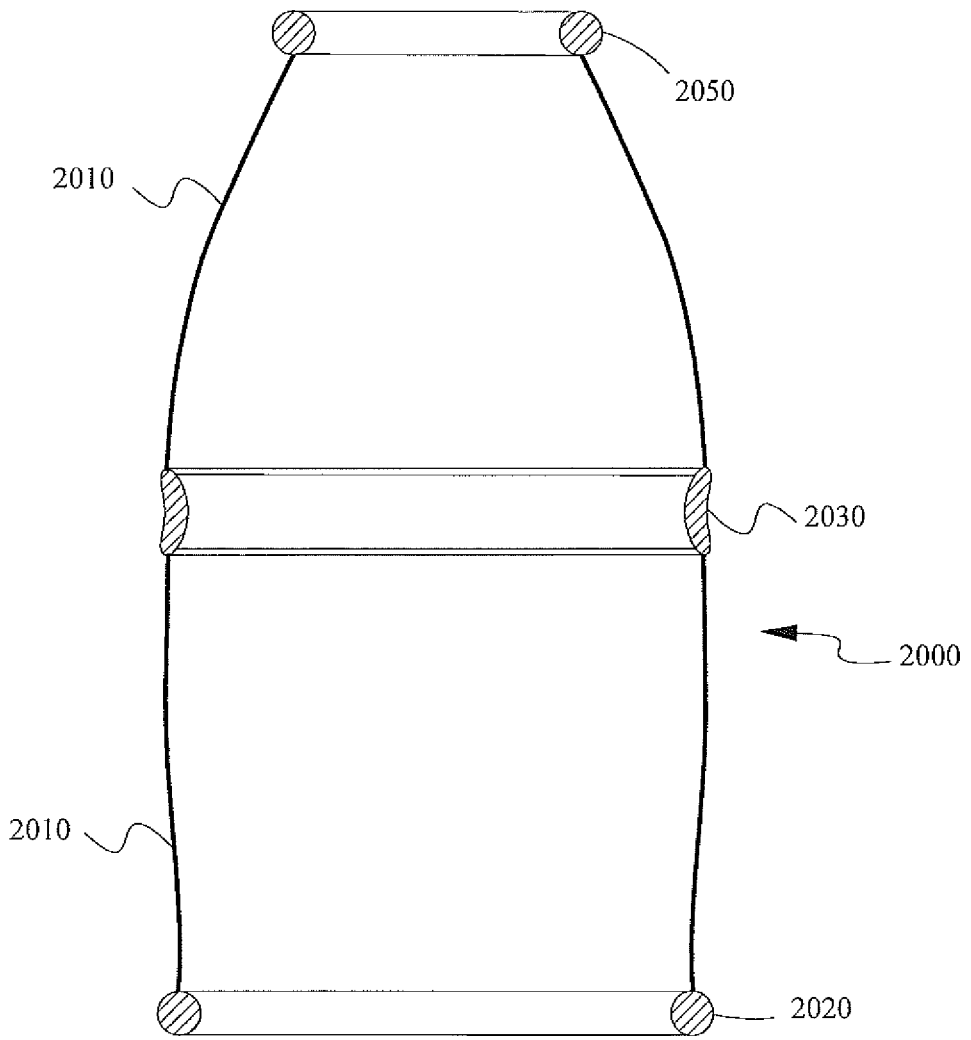
FIG. 10 is a longitudinal cross-sectional view of an access port of the surgical access assembly of FIG. 9.
Figure 11:
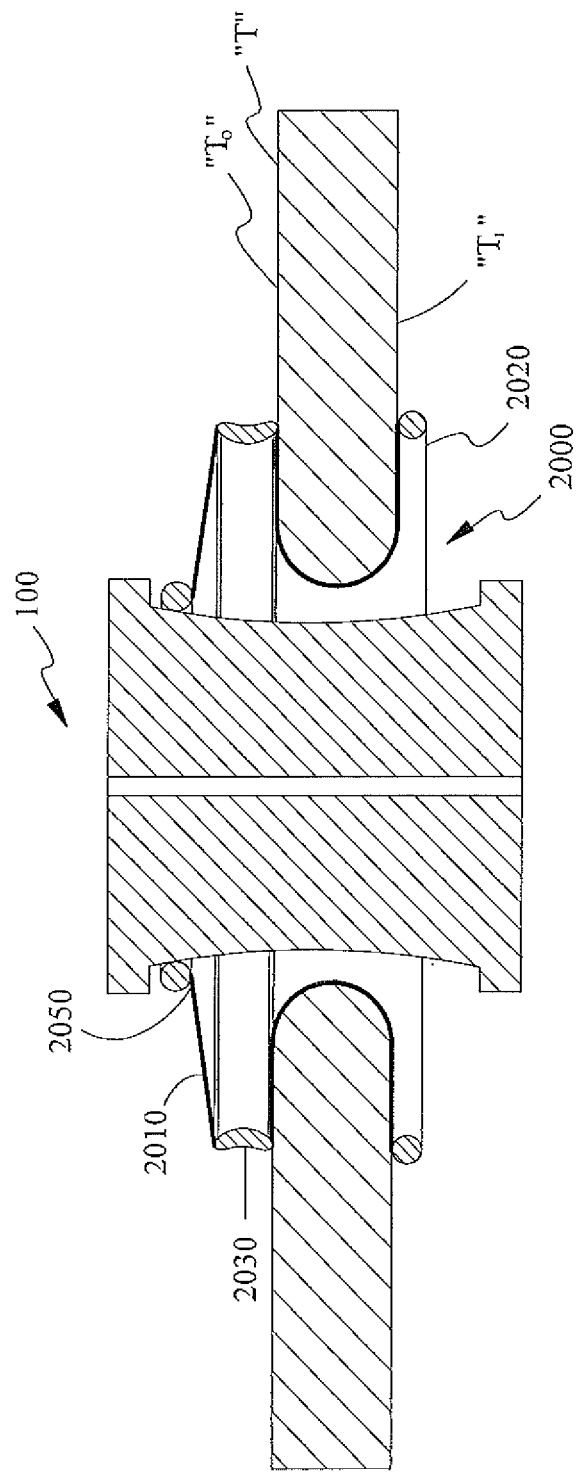
FIG. 11 is longitudinal cross-sectional view of the access assembly of FIG. 9 secured to tissue.
Figure 12:
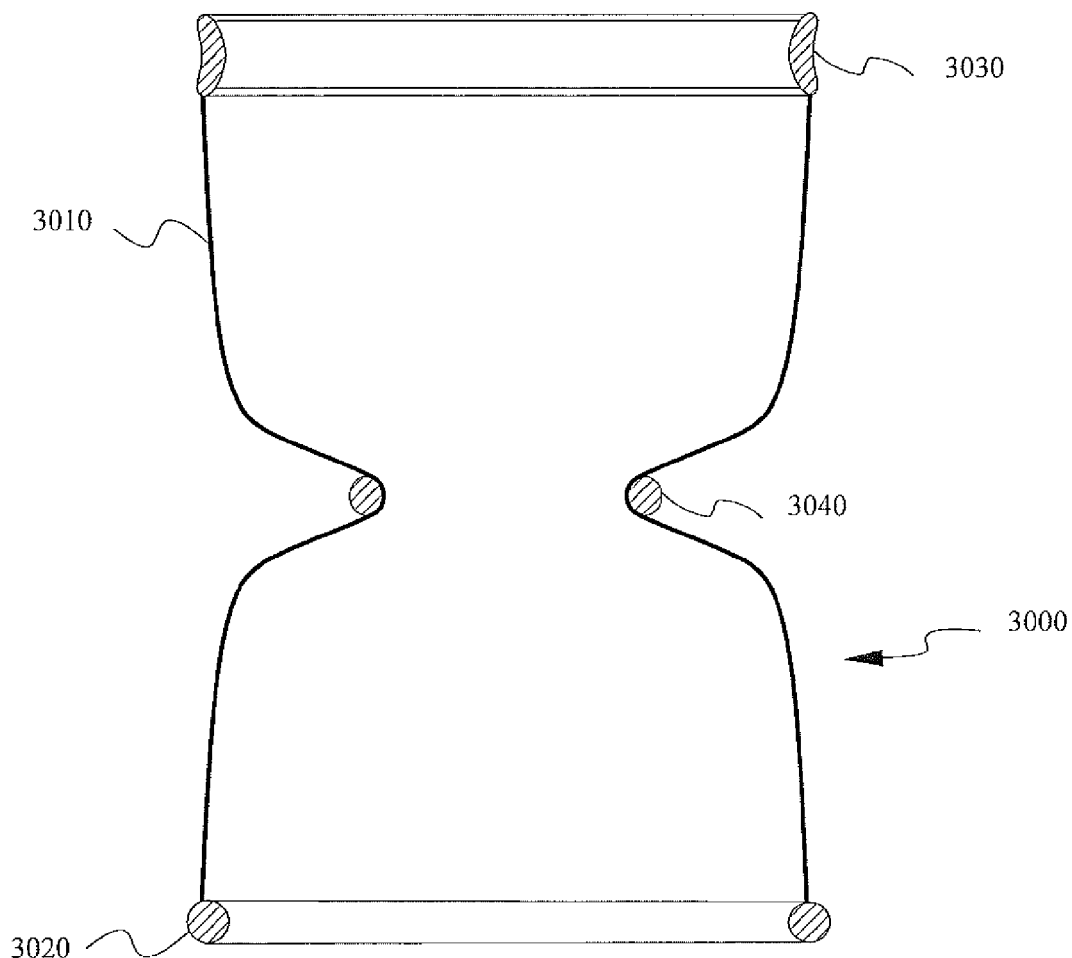
FIG. 12 is an access port in accordance with an embodiment of the present disclosure.

With reference now to FIGS. 9-11, an access assembly 20 in accordance with still another embodiment of the present disclosure is illustrated. In the interest of brevity, the present embodiment will focus on the differences between access assembly 20 and the previously described access assembly 10. Access assembly 20 includes an access port 2000 and seal anchor 200. Access port 2000 includes a proximal ring 2050, an intermediate ring 2030, a distal ring 2020 and a flexible sleeve 2010 defining a passage therethrough. Proximal, intermediate and distal rings 2050, 2030, 2020 are concentrically arranged and are longitudinally connected to sleeve 2010.

Proximal ring 2050 is adapted to engage intermediate portion 206 of seal anchor 200. In particular, proximal ring 2050 is dimensioned to engage circumferential groove 250 defined in intermediate portion 206 adjacent proximal end portion 202 of seal anchor 200. In order to provide an appropriate sealing relation with intermediate portion 206 of seal anchor 200, proximal ring 2050 may include a diameter smaller than that of intermediate portion 206.

With particular reference to FIG. 10, intermediate member 2030 may have a kidney-shaped cross-sectional profile. Kidney-shaped cross-sectional profile facilitates rolling of sleeve 2010 about intermediate ring 2030 and inhibits unrolling of sleeve 2010 over intermediate ring 2030 by providing a flattened edge disposed on the outer epidermal tissue $T_O$. Proximal and distal rings 2050, 2020, on the other hand, may each be an O-ring having a circular cross-section. However, other cross-sectional profiles are also contemplated for proximal, intermediate, and distal rings 2050, 2030, 2020. It is also envisioned that the O-ring may be an inflatable balloon.

In addition, intermediate and distal rings 2030, 2020 can vary in size. For example, dimensions of intermediate and distal rings 2030, 2020 may be selectively chosen to be greater than that of the opening in tissue "T" (FIG. 11). In this manner, intermediate and distal rings 2030, 2020 may have sufficient footing to maintain elastic sleeve 2010 that has been stretched and retained at a distance greater than the natural distance. In addition, by having dimensions of intermediate and distal rings 2030, 2020 larger than that of the opening, access port 2000 is adapted to dilate the opening to a desired dimension. More retraction is possible through shortening of sleeve 2010 by rolling proximal ring 2030, e.g., outward, while less retraction is possible by rolling proximal ring 2050, e.g., inward.

In contrast to access port 1000, intermediate and distal rings 2030, 2020 of access port 2000 provide securement against tissue "T." Specifically, intermediate ring 2030 engages the outer epidermal tissue $T_O$ adjacent the incision in tissue "T," and distal ring 2020 positioned in the body cavity engages the internal peritoneal wall $T_I$. Proximal ring 2050 engages intermediate portion 206 of seal anchor 200 to provide a fluid-tight seal therewith. In further contrast to access port 1000, a portion of sleeve 2010 that connects proximal ring 2050 and intermediate ring 2030 to provide a fluid-tight seal between a body cavity of a patient and the atmosphere is exposed to the atmosphere. Proximal ring 2050 providing a fluid-tight seal against intermediate portion 206 of seal anchor 200 is exposed to the atmosphere and is out of the body cavity. Such configuration enables the user to easily adjust the position of proximal ring 2050 with respect to intermediate portion 206 of seal anchor 200. The use and operation of access port 2000 is substantially similar to that of access port 1000 discussed hereinabove, and thus will not be described herein.

With reference now to FIGS. 12-15, an access port 3000 in accordance with another embodiment of the present disclosure is illustrated. In the interest of brevity, the present embodiment will focus on the differences between access port 3000 and the previously described access ports 1000, 2000. Access port 3000 includes a proximal ring 3030, an intermediate ring 3040, a distal ring 3020 and a flexible sleeve 3010 defining a passage therethrough. Proximal, intermediate and distal rings 3030, 3040, 3020 are concentrically arranged with respect to the passage of sleeve 3010. Sleeve 3010 extends between proximal ring 3030 and distal ring 3020 and is attached thereto. Intermediate ring 3040 is slidably disposed around an outer surface of sleeve 3010 between proximal and distal rings 3030, 3020.

Figure 14:
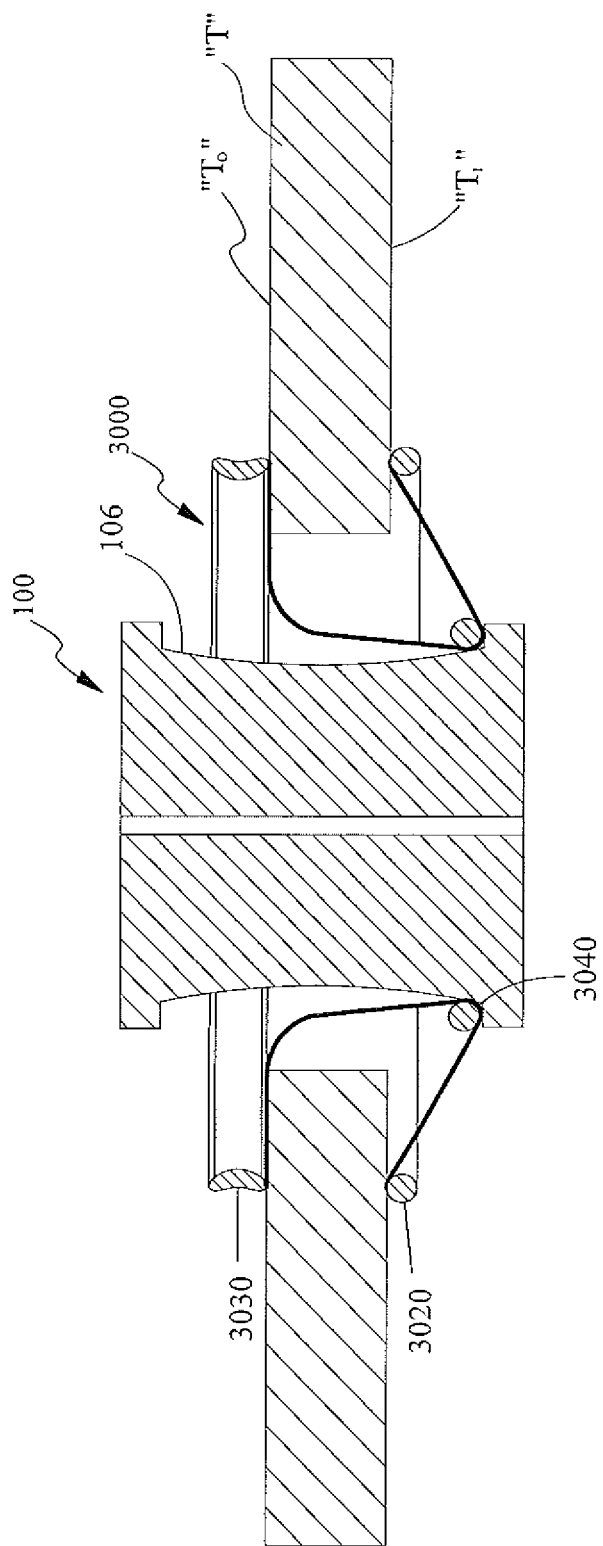

In particular, proximal ring 3030 may have kidney-shaped cross-sectional profile. Kidney-shaped cross-sectional profile facilitates rolling of sleeve 3010 about proximal ring 3030 and inhibits unrolling of sleeve 3010 over proximal ring 3030. Proximal ring 3030 is adapted to engage the outer epidermal tissue $T_O$, and a distal ring 3020 is adapted to engage the internal peritoneal wall $T_I$ (FIG. 14). Intermediate ring 3040 is adapted to provide a fluid-tight seal against sleeve 3010 and seal anchor 100. Intermediate ring 3040 may be disposed beneath tissue "T" (as illustrated in FIG. 14) or may be exposed to the atmosphere.

The diameter of intermediate ring 3040 is smaller than that of proximal and distal rings 3030, 3040 to slidably retain intermediate ring 3040 between proximal and distal rings 3030, 3040 on the outer surface of sleeve 3010. Furthermore, the diameter of intermediate ring 3040 may be smaller than that of intermediate portion 106 of seal anchor 200 to facilitate fluid-tight seal against seal anchor 100.

The dimensions of proximal and distal rings 3030, 3020 is selectively chosen to be greater than that of the opening in tissue "T" (FIG. 14). In this manner, proximal and distal rings 3030, 3020 may have sufficient footing to maintain elastic sleeve 3010 that has been stretched and retained at a distance greater than the natural distance. In addition, by having dimensions of proximal and distal rings 3030, 3020 larger than that of the desired working channel, access port 3000 is adapted to dilate the opening to a desired dimension. More retraction is possible through shortening of sleeve 3010 by rolling proximal ring 3030 outward, while less retraction is possible by rolling proximal ring 3030 inward.

Figure 13:
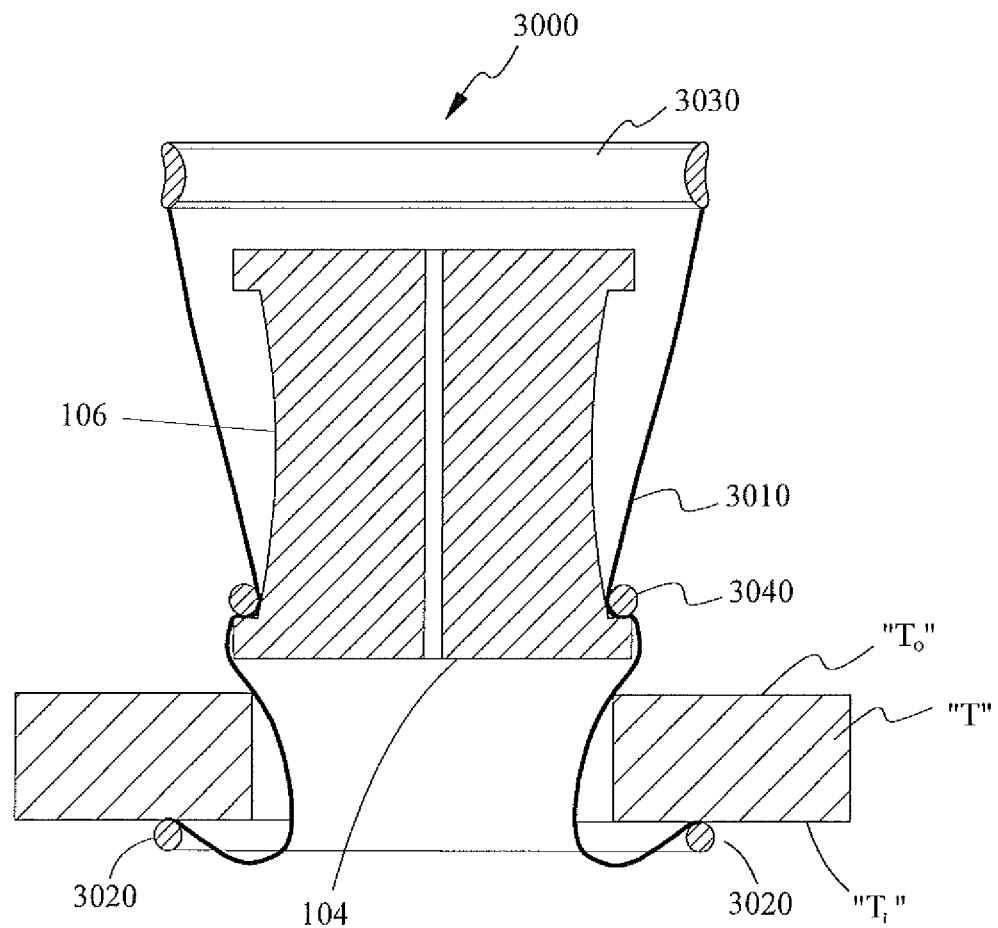
FIGS. 13 and 14 are longitudinal cross-sectional views of a surgical access assembly including the access port of FIG. 12 illustrating securement thereof to tissue.

In contrast to access ports 1000, 2000, access port 3000 provides slidably adjustable intermediate ring 3040. While FIGS. 13 and 14 illustrate intermediate ring 3040 disposed on intermediate portion 106 adjacent distal end portion 104 of seal anchor 100, intermediate ring 3040 may be adjustably disposed along any longitudinal position along intermediate portion 106 of seal anchor 100.

Figure 15:
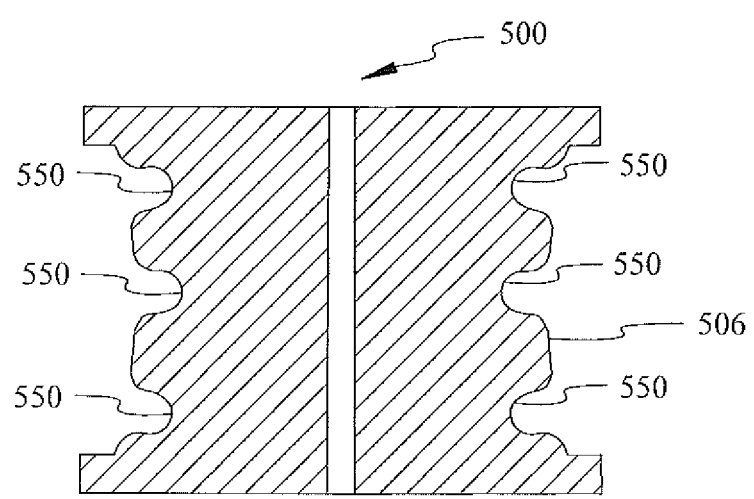
FIG. 15 is a longitudinal cross-sectional view of a seal anchor in accordance with an embodiment of the present disclosure for use with the access port of FIG. 12.

With reference now to FIG. 15, there is shown a seal anchor 500 for use with access port 3000. It is contemplated that seal anchor 500 may include an intermediate portion 506 defining a plurality of circumferential grooves 550 in tandem (FIG. 15). Each circumferential groove 550 is dimensioned and configured to receive therein longitudinally adjustable intermediate ring 3040. Intermediate ring 3040 may engage, for example, circumferential groove 550 defined adjacent a proximal end portion of seal anchor 500. The use and operation of access port 3000 is substantially similar to that of access ports 1000, 2000 discussed hereinabove. Thus, the operation and use of access port 3000 will not be discussed herein in the interest of brevity.

Although the illustrative embodiments of the present disclosure have been described herein with reference to the accompanying drawings, the above description, disclosure, and figures should not be construed as limiting, but merely as exemplifications of particular embodiments. It is to be understood, therefore, that the disclosure is not limited to those precise embodiments, and that various other changes and modifications may be effected therein by one skilled in the art without departing from the scope or spirit of the disclosure.

What is claimed is:

1. A surgical access assembly comprising:
an access port including a proximal ring, an intermediate ring, a distal ring, and a sleeve defining a passage therethrough, the sleeve extending between the proximal and distal rings, the proximal ring being rollable to adjust a length of the sleeve, the proximal ring having a non-circular cross-section; and
a seal anchor having a proximal end, a distal end, and an intermediate portion extending between the proximal and distal ends, the seal anchor adapted to be at least partially disposed in the access port, the seal anchor defining a lumen therethrough, wherein the distal ring is configured and dimensioned to engage the intermediate portion of the seal anchor in a sealing relation therewith, the seal anchor having a diameter larger than a diameter of the distal ring, the diameter of the seal anchor that is larger than the diameter of the distal ring is dimensioned to be received through the proximal and intermediate rings such that the distal ring and a portion of the seal anchor are adapted to be disposed beneath an outer surface of a tissue.

2. The surgical access assembly according to claim 1, wherein at least one of the distal or intermediate rings is an O-ring.

3. The surgical access assembly according to claim 2, wherein the O-ring is an inflatable balloon.

4. The surgical access assembly according to claim 1, wherein the seal anchor defines an hourglass shape.

5. The surgical access assembly according to claim 1, wherein at least one of the proximal, distal, or intermediate rings is elastic.

6. The surgical access assembly according to claim 1, wherein the proximal ring has a kidney-shaped cross-section.

7. The surgical access assembly according to claim 1, wherein the sleeve is formed of an elastic material.

8. The surgical access assembly according to claim 1, wherein the seal anchor is formed of a compressible material.

9. The surgical access assembly according to claim 1, wherein the lumen of the seal anchor is dimensioned to receive a surgical instrument therethrough.

10. The surgical access assembly according to claim 1, wherein at least one of the proximal, distal, or intermediate rings is an inflatable balloon.

11. The surgical access assembly according to claim 1, wherein the seal anchor defines a circumferential groove dimensioned to receive one of the proximal, intermediate, or distal rings.

12. A method of accessing an internal body cavity, comprising:
providing a surgical access assembly including:
an access port having a proximal ring, an intermediate ring, a distal ring, and a sleeve defining a passage extending through the proximal, intermediate, and distal rings; and
a seal anchor having a proximal end, a distal end, and an intermediate portion extending between the proximal and distal ends, the seal anchor adapted to be at least partially disposed in the access port;
positioning the intermediate ring of the access port into the internal body cavity;
rolling the proximal ring such that the proximal ring engages an outer epidermal tissue and the intermediate ring engages an internal peritoneal wall of tissue; and
positioning at least a portion of the seal anchor within the access port such that the distal ring engages the intermediate portion of the seal anchor in a seal relation therewith.

13. The method of accessing the internal body cavity according to claim 12, wherein rolling the proximal ring includes rolling the proximal ring having a non-circular cross-section.

14. The method of accessing the internal body cavity according to claim 13, wherein rolling the proximal ring includes rolling the proximal ring having a kidney-shaped cross-section.

15. The method of accessing the internal body cavity according to claim 12, further comprising insufflating the internal body cavity.

16. The method of accessing the internal body cavity according to claim 12, further comprising introducing a surgical instrument into the internal body cavity through the seal anchor.

17. The surgical access assembly according to claim 1, wherein the sleeve connects the proximal, intermediate, and distal rings, such that the access port is formed as a single construct.

* * * * *